United States Patent [19]

Morancais et al.

[11] Patent Number: 5,626,868
[45] Date of Patent: May 6, 1997

[54] COSMETIC AND/OR PHARMACEUTICAL COMPOSITION CONTAINING A DISPERSION OF LIPID VESICLES, PROCESS FOR THE PREPARATION OF THE SAID DISPERSION AND DISPERSION OF LIPID VESICLES

[75] Inventors: Jean-Luc Morancais, Ozoir-La-Ferriere; Alain Lety, Lagny-Sur-Marne; Guy Vanlerberghe, Villevaude, all of France

[73] Assignee: L'Oreal, Paris, France

[21] Appl. No.: 385,552

[22] Filed: Feb. 8, 1995

Related U.S. Application Data

[63] Continuation of Ser. No. 133,140, filed as PCT/FR93/00128, Feb. 8, 1993, Pat. No. 5,443,840.

[30] Foreign Application Priority Data

Feb. 18, 1992 [FR] France ................................. 92 01821

[51] Int. Cl.$^6$ ................................. A61K 9/127
[52] U.S. Cl. .................. 424/450; 424/401; 428/402.2; 514/944
[58] Field of Search .................. 424/450, 401; 428/402.2; 514/944

[56] References Cited

U.S. PATENT DOCUMENTS

| | | | |
|---|---|---|---|
| 4,694,084 | 9/1987 | Breuniger | 424/450 |
| 4,900,545 | 2/1990 | Wisotzki | 424/450 |
| 5,041,283 | 8/1991 | Kita | 424/450 |
| 5,137,725 | 8/1992 | Handjani | 424/450 |
| 5,192,544 | 3/1993 | Grollier | 424/450 |
| 5,234,767 | 8/1993 | Wallach | 424/450 |
| 5,268,180 | 12/1993 | Morancais | 424/450 |

FOREIGN PATENT DOCUMENTS

| | | |
|---|---|---|
| A3154977 | 9/1985 | European Pat. Off. |
| A1287876 | 10/1988 | European Pat. Off. |
| B1154977 | 5/1989 | European Pat. Off. |
| A3343444 | 11/1989 | European Pat. Off. |
| A1422978 | 4/1991 | European Pat. Off. |
| A1423011 | 4/1991 | European Pat. Off. |
| A14444983 | 9/1991 | European Pat. Off. |
| B1343444 | 1/1992 | European Pat. Off. |
| B1287876 | 1/1993 | European Pat. Off. |

| | | |
|---|---|---|
| 2189457 | 10/1987 | United Kingdom. |
| 8706460 | 11/1987 | WIPO. |

OTHER PUBLICATIONS

Yue et al, "Deuterium NMR study of the magnetic orientation.", Biochem. Biophys. Acta, Lipids and Lipid Metabolism, vol. 1047, No. 1, 1990, pp. 1–10.

Cushley et al, "Structure and stability of vitamin E–lecithin and phytanic acid–lecithin bilayers studied by 13C and 31P nuclear magnetic resonance", Can. J. Chem. vol. 55, No. 2, 1977, pp. 220–226.

Roding, "Natipide II: New easy liposome system", Seifen—Ole—Fette—Wachse, 116, No. 14, 1990.

*Primary Examiner*—Gollamudi S. Kishore
*Attorney, Agent, or Firm*—Cushman Darby & Cushman Intellectual Property Group of Pillsbury Madison & Sutro LLP

[57] ABSTRACT

A composition comprises in an aqueous dispersion phase, a dispersion of lipid vesicles that encapsulate an aqueous phase. The lipid vesicles are a lipid phase containing an ionic amphiphilic lipid or a nonionic amphiphilic lipid, or a mixture thereof, together with a compound having the formula

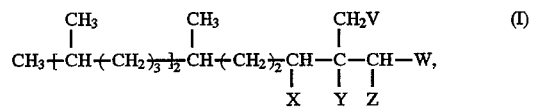

wherein (a) W represents —CH$_2$OH, —COOM or —(CH$_2$)$_2$—COOM, wherein M represents H, alkali metal or alkaline earth metal and X, Y, Z and V, each independently, represent hydrogen or hydroxyl, with the proviso that when W represents —CH$_2$OH at least one of X, Y, Z or V represents hydroxyl, or (b) W represents —CH$_3$ and X, Y, Z and V represent H or OH combined as shown in each line of the table below:

| X | Y | Z | V |
|---|---|---|---|
| OH | OH | OH | OH |
| OH | H | OH | OH |
| OH | OH | OH | H |
| H | OH | OH | OH |
| H | OH | OH | H |
| H | H | OH | OH |
| OH | H | OH | H |

15 Claims, No Drawings

COSMETIC AND/OR PHARMACEUTICAL COMPOSITION CONTAINING A DISPERSION OF LIPID VESICLES, PROCESS FOR THE PREPARATION OF THE SAID DISPERSION AND DISPERSION OF LIPID VESICLES

This is a continuation of application Ser. No. 08/133,140, filed as PCT/FR93/00128, Feb. 8, 1993, now U.S. Pat. No. 5,443,840.

The present invention relates to a cosmetic and/or pharmaceutical composition containing a transparent dispersion of ionic and/or nonionic amphiphilic lipid vesicles, to a process for the preparation of said dispersion and to a new dispersion used in the said composition.

It is known that it is possible to prepare vesicles from certain amphiphilic lipids, that is to say from molecules consisting of a lipophilic part and of a hydrophilic part. The vesicles obtained are delimited by a lipid phase membrane formed from a sheet or a number of concentric sheets, the said membrane defining a closed internal volume where a phase, known as encapsulated phase, is encapsulated. The vesicles are generally prepared in the form of a dispersion in an aqueous phase, known as the dispersion phase. The amphiphilic lipids can be ionic lipids such as natural lecithins (egg lecithin, soya lecithin) or synthetic lecithins (dipalmitoyl-lecithin, hydrogenated egg lecithin). The amphiphilic lipids can also be nonionic lipids such as linear or branched polyglycerol derivatives, linear or branched polyglycerol ethers, polyoxyethylenated fatty alcohols, polyoxyl-ethylenated sterols, polyol ethers, oxyethylenated or nonoxyethylenated polyol esters, glycol lipids, certain hydroxyamides and others.

The lipid phase can contain one or a number of ionic amphiphilic lipids, one or a number of nonionic amphiphilic lipids or, at the same time, at least one ionic amphiphilic lipid and at least one nonionic amphiphilic lipid.

It is known to introduce into the lipid phase at least one lipophilic cosmetically and/or pharmaceutically active principle, the nature and the amount of the reactants introduced being chosen so as not to damage the stability of the vesicles. It is also possible, in a known way, to introduce hydrophilic active principles into the encapsulated aqueous phase and/or into the aqueous dispersion phase.

For reasons of presentation, the search is to prepare dispersions of vesicles which are substantially transparent, because the cosmetic compositions prepared from transparent dispersions have a more pleasant and more attractive appearance for the user.

The transparency (or, conversely, the opaqueness) of a dispersion, with respect to natural light, is essentially a function of the refractive index of the dispersion medium and of that of the dispersion particles, of the concentration, of the mean size and of the size homogeneity of these particles. It is especially possible to increase the transparency of a dispersion by reducing the difference between the refractive index of the dispersed particles and that of the dispersion medium and/or by reducing the concentration and/or the size of the dispersed particles. Of course, it is possible to improve the transparency of a dispersion of lipid vesicles by diluting this dispersion but the concentration of active principles in the dispersion would thus be reduced, which generally has to be avoided. It has also been attempted to reduce the mean size of the vesicles, but it is then necessary to use, for an excessively long time, during the preparation of the vesicles, powerful mechanical means such as pressure homogenizers or ultrasound, which leads to a higher cost price. It was also considered to reduce the polydispersity by using grading methods such as pressure filtration or size fractionation using chromatography columns, but these methods are restricting and expensive.

According to the present invention, it was found that the transparency of dispersions of vesicles in which the lipid phase contains at least one ionic amphiphilic lipid and/or at least one nonionic amphiphilic lipid is considerably improved by introducing, into the said lipid phase, at least one polyol or one isoprenoic acid containing a phytyl chain, without it being necessary to modify the method of preparation of the vesicles. It was observed that even dispersions having a high lipid concentration, for example a concentration greater than 5% by weight, are then substantially transparent.

The first subject of the present invention is thus a cosmetic and/or pharmaceutical composition containing at least one dispersion, in an aqueous dispersion phase, of vesicles delimited by a lipid phase membrane containing at least one ionic amphiphilic lipid and/or at least one nonionic amphiphilic lipid, the said vesicles containing an encapsulated phase, characterized in that, in at least one dispersion, the lipid phase contains at least one compound of formula

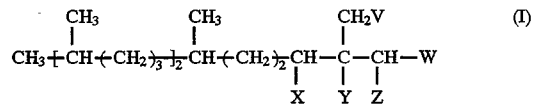

in which formula (I):

either W represents —$CH_2OH$, —COOM or —$(CH_2)_2$—COOM, where M represents H, an alkali metal or an alkaline-earth metal, in which case X, Y, Z and V, which are identical or different, represent a hydrogen atom or a hydroxyl radical, with the condition that, when W represents the —$CH_2OH$ group, at least one of the radicals X, Y, Z or V represents a hydroxyl radical;

or else W represents the —$CH_3$ group, in which case X, Y, Z and V represent H or —OH combined as shown in each line of the table below:

| X  | Y  | Z  | V  |
|----|----|----|----|
| OH | OH | OH | OH |
| OH | H  | OH | OH |
| OH | OH | OH | H  |
| H  | OH | OH | OH |
| H  | OH | OH | H  |
| H  | H  | OH | OH |
| OH | H  | OH | H  |

The compounds of formula (I), which are preferred, are phytanetriol or 3,7,11,15-tetramethyl-1,2,3-trihydroxyhexadecane, 5,9,13,17-tetramethyloctadecanoic acid or the tetrols such as 3,7,11,15-tetramethyl-1,2,3,4-tetrahydroxyhexadecane or 3-hydroxymethyl-7,11,15-trimethyl-1,2,4-trihydroxyhexadecane obtained as by-products in the synthesis of phytanetriol by oxidation of phytol with hydrogen peroxide.

As explained above, the first advantage of the dispersions of the composition according to the invention is that these dispersions are transparent, even for high lipid concentrations.

Moreover, it was observed that, in the case of the preparation of certain vesicles, the introduction of at least one compound of formula (I) into the lipid phase made it possible to reduce or eliminate cholesterol, which is commonly used as constituent lipid of the wall of the vesicles, with the aim of stabilizing the vesicles. The replacement of cholesterol by a (some) compound(s) of formula (I) is of substantial advantage because the compounds of formula (I) are very difficult to oxidize, whereas cholesterol oxidizes relatively easily giving undesirable oxidation products. Moreover, the dispersions used according to the invention are generally obtained directly with a low polydispersity index without it being necessary, during their preparation, to resort to an expensive fractionation. Finally, it was observed that the topical application of certain of the dispersions makes it possible to reduce the modulus of elasticity of the stratum corneum, which is very particularly advantageous in cosmetics.

The compounds of formula (I) are known compounds (see, for example, "Progress in the chemistry of fats and other lipids", Volume XIV, Part 1, pages 5 to 44, Ak Lough, Editor Ralph T. Holman, Pergamon Press). It is known, by an article by Yue et al. (Biochimica et Biophysica Acta, Vol. 1047, No. 1, pages 1–102), to prepare a dispersion of vesicles from a lipid phase containing phospholipids, in particular dipalmitoylphosphatidylcholine, and phytanic acid in order to study the influence of phytanic acid on the phospholipid layer, by nuclear magnetic resonance. This study shows that the presence of phytanic acid in the vesicle membrane causes a reorientation of the phospholipid layers in the magnetic field. According to an article by R. J. Cushley et al. (Can. J. of Chemistry, Vol. 55, 1977, pages 220–226), the introduction of phytanic acid into the lipid phase of lecithin vesicles would greatly destabilize the structure of the vesicle membrane. It has also been proposed to use phytanetriol in cosmetics (see CH-A 399,655, JP-A 63/5050 and JP-A 86/236,737).

However, until the present, the use of a vesicle dispersion containing compounds of formula I in cosmetic and/or pharmaceutical compositions has never been proposed and nothing could suggest to a person skilled in the art the specific advantages of such a use, in particular that the dispersions obtained would be transparent.

In the lipid phase constituting the membrane of the vesicles, the compounds of formula (I) represent, by weight, from 5 to 90%, and preferably from 10 to 60%, of the lipid phase. For amounts below 5%, there is no significant improvement in the transparency. For amounts greater than 90%, the vesicles obtained are no longer stable enough.

The constituent lipid phase of the membranes of the vesicles of the dispersion according to the invention can comprise, in a known way, at least one lipid chosen from the group formed by:

A) the nonionic lipids defined below:

(1) the linear or branched glycerol derivatives of formula $$R_0O-(C_3H_5(OH)O)_{\overline{n}}H \qquad (II)$$

in which formula (II):

—$C_3H_5(OH)O$— is represented by the following structures taken as mixtures or separately:

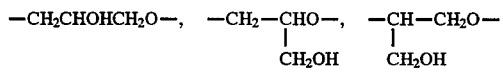

$\overline{n}$ is a mean statistical value between 1 and 6 or else n=1 or 2 and then —$C_3H_5(OH)O$— is represented by the structure —$CH_2CHOH$—$CH_2O$—;

$R_o$ represents:

(a) a saturated or unsaturated, linear or branched, aliphatic chain containing from 12 to 30 carbon atoms; or hydrocarbon radicals from lanolin alcohols; or the residues of long-chain alpha-diols;

(b) a residue $R_1CO$, where $R_1$ is a linear or branched, $C_{11}$–$C_{29}$ aliphatic radical;

(c) a residue $$R_2+OC_2H_3(R_3)+$$

where:

$R_2$ can take the meaning (a) or (b) given for $R_0$;

—$OC_2H_3(R_3)$— is represented by the following structures, taken as a mixture or separately:

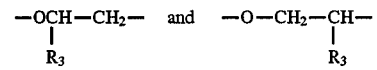

where $R_3$ takes the meaning (a) given for $R_0$;

(2) the linear or branched polyglycerol ethers containing two fatty chains;

(3) the diols containing a fatty chain;

(4) the oxyethylenated or nonoxyethylenated fatty alcohols, or the oxyethylenated or nonoxyethylenated phytosterols or sterols, such as, for example, cholesterol;

(5) the oxyethylenated or nonoxyethylenated ethers and esters of polyols, it being possible for the ethylene oxide chain to be linear or cyclic;

(6) the glycolipids of natural or synthetic origin, the ethers and esters of mono- or polysaccharides and especially the ethers and the esters of glucose;

(7) the hydroxyamides described in French Patent No. 2,588,256 and represented by the formula:

$$R_4-CHOH-CH-COA \qquad (III)$$
$$\phantom{R_4-CHOH-CH}| $$
$$\phantom{R_4-CHOH-}R_5-CONH$$

in which formula (III):

$R_4$ denotes a $C_7$–$C_{21}$ alkyl or alkenyl radical;

$R_5$ denotes a saturated or unsaturated $C_7$–$C_{31}$ hydrocarbon radical;

COA denotes a group chosen from the two following groups:

a residue

where:

B is an alkyl radical derived from mono- or polyhydroxylated, primary or secondary amines; and $R_6$ denotes a hydrogen atom or a methyl, ethyl or hydroxyethyl radical; and a residue —COOZ, where Z represents the residue of a $C_3$–$C_7$ polyol.

(8) the natural or synthetic ceramides;

(9) the oxyethylenated fatty amines or dihydroxyalkylamines;

(10) the glycerol derivatives described in Patent Application PCT No. 91/00889 filed on 13 Nov. 1991 and corresponding to the formula:

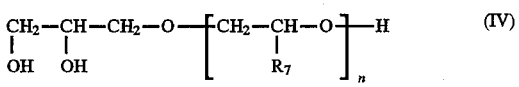

in which formula (IV) $R_7$ represents a linear $C_{14}$ to $C_{18}$ alkyl radical or a group —$CH_2A$ in which A is —$OR_{14}$, $R_{14}$ representing a linear $C_{10}$–$C_{18}$ alkyl radical and, preferably, a linear $C_{16}$ alkyl radical, and n represents a mean statistical value greater than 1 and at most equal to 3 and, additionally, when $R_7$=—$CH_2A$, n can also represent a true value (non-statistical) equal to 2.

B) the ionic amphiphilic lipids defined below:
(1) the anionic amphiphilic lipids such as:
   the natural phospholipids, especially egg or soya lecithin, or sphingomyelin, the phospholipids modified chemically or enzymatically, especially hydrogenated lecithin, and the synthetic phospholipids, especially dipalmitoylphosphatidylcholine;
   anionic compounds, such as those described in French Patent No. 2,588,256 and represented by the formula

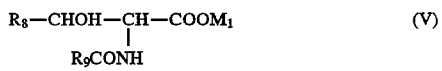

in which formula (V):
$R_8$ represents a $C_7$–$C_{21}$ alkyl or alkenyl radical,
$R_9$ represents a saturated or unsaturated $C_7$–$C_{31}$ hydrocarbon radical, and
$M_1$ represents H, Na, K, $NH_4$ or a substituted ammonium ion derived from an amine,
(2) anionic compounds, such as the phosphoric esters of fatty alcohols, for example dicetyl phosphate and dimyristyl phosphate in the form of acids or of alkaline salts; heptylnonylbenzenesulfonic acid; cholesterol acid sulfate and its alkaline salts and cholesterol acid phosphate and its alkaline salts; lysolecithins; alkyl sulfates, for example sodium cetyl sulfate; gangliosides;
(3) the cationic amphiphilic lipids, such as:
   the quaternary ammonium derived cationic compounds corresponding to the formula:

with $R_{10}$ and $R_{11}$, which are identical or different, representing $C_{12}$–$C_{20}$ alkyl radicals and $R_{12}$ and $R_{13}$, which are identical or different, $C_1$–$C_4$ alkyl radicals;
   the long-chain amines and their quaternary ammonium derivatives, and the long-chain amino alcohol esters and their salts and quaternary ammonium derivatives;
   polymerizable lipids, such as those described by Ringsdorf and others in "Angewandte Chemie", Vol. 27, No. 1, January 1988, pages 129 and 137.

The amphiphilic lipids used together represent preferably from 10 to 95%, more particularly from 40 to 90%, of the total weight of the vesicular lipid phase.

Non-lipid additives such as certain polymers, such as, for example, polypeptides and proteins, can be added to the lipid phase constituting the wall of the vesicles.

The aqueous dispersion phase according to the invention can consist of water, or a mixture of water and at least one water-miscible solvent such as $C_1$–$C_7$ alcohols and $C_1$–$C_5$ alkyl polyols. The aqueous dispersion phase can also contain compounds in solution, such as sugars, organic or inorganic salts or polymers insofar as they do not modify or only slightly modify the transparency of the dispersion.

The total lipid phase concentration in the dispersion is between 0.01% and 50% by weight, preferably between 1% and 20% by weight, with respect to the total weight of the dispersion. The dispersed vesicles have sizes between 20 and 3000 nm, preferably between 20 and 500 nm.

The compositions according to the invention can be used even in the absence of any active principle, as cosmetic products for skin treatment. It has especially been observed that, when the compound of formula (I) is phytanetriol, topical application of the composition makes it possible to reduce the modulus of elasticity of the stratum corneum.

However, the compositions according to the invention can also contain at least one active principle having cosmetic and/or pharmaceutical action.

In a known way, it is possible to introduce into the lipid phase of the vesicles of the dispersion at least one cosmetically and/or pharmaceutically active liposoluble compound. According to the invention, it is possible to use any liposoluble active principle insofar as it is compatible with the compounds of formula (I) used and insofar as it does not modify in a harmful way the transparency of the compositions. Among the latter, there may be mentioned as non-limiting examples: retinoic acid, lipoprotides and steroids.

The phase encapsulated in the vesicles is generally an aqueous phase. In a known way, water-soluble active principles can be introduced into the encapsulated phase and/or into the dispersion phase. Very many compounds of this type have been mentioned in the literature. Among the latter, there may be mentioned as non-limiting examples: glycerol, sorbitol, erythrulose and antibiotics.

Amphiphilic active principles can also be distributed between the encapsulated and/or dispersion aqueous phase and the lipid phase of the vesicles.

A list of the active principles which can be used in the compositions according to the invention is given in Table I below:

TABLE I

| FUNCTION | ACTIVE AGENTS WHICH ARE USABLE |
|---|---|
| Antioxidant or anti-free-radicals | The extracts of the following plants: Hawthorn. Ginkgo biloba. Green tea. Vine. Rosemary. |

TABLE I-continued

| FUNCTION | ACTIVE AGENTS WHICH ARE USABLE |
|---|---|
| | Enzymes: |
| | Marketed by SEDERMA under the name SB 12, and consisting of a mixture of lactoferrin and lactoperoxidase, glucose oxidase and potassium thiocyanate. |
| | Superoxide dismutase. |
| | Glutathione peroxidase. |
| | Superphycodismutase extracted from algae. |
| | Coenzymes Q, especially coenzyme Q10. |
| | Sequestering agents, especially polyphosphonic acid derivatives. |
| | Tannins. |
| | Selenium and its derivatives, especially seleno methionine. |
| | Peptides, for example a mixture of spleen and thymus extracts, Thiolim and unstabilized bovine serum albumin. |
| | Proteins, for example hemocyanin, which is a copper-containing protein extracted from marine snails, and apohemocyanin, which is a similar protein without copper. |
| | Flavonoids, in particular catechin, proantho-cyanidins, flavanols, flavones, isoflavones, flavanenols, flavanones, flavanes and chalcones. |
| | Carotenoids, in particular β-carotene and annatto. |
| | Sorbohydroxyamic acid. |
| | Tocopherols, in particular alpha-tocopherol and alpha-tocopherol acetate. |
| | Ascorbyl palmitate. |
| | Propyl gallate. |
| | Caffeic acid and its derivatives. |
| | Ascorbic acid. |
| | Homogentisic acid. |
| | Erythorbic acid. |
| | Nordihydroguaiacetic [sic] acid. |
| | Lysine laurylmethionate. |
| | Butylated hydroxyanisole. |
| | Butylated hydroxytoluene. |
| | "SOD-like" substances. |
| Hydrating or humectant | A reconstitution of sweat ("Normal moisturizing factors" - NMF). |
| | Sodium pyroglutamate. |
| | Hyaluronic acid. |
| | Chitosan derivatives (carboxymethylchitin). |
| | β-Glycerophosphate. |
| | Lactamide. |
| | Acetamide. |
| | Ethyl, sodium and triethanolamine lactates. |
| | Metal pyrrolidonecarboxylates, especially those of Mg, Zn, Fe, Ca or Na. |
| | Thiamorpholinone. |
| | Orotic acid. |
| | alpha-hydroxylated $C_3$ to $C_{20}$ carboxylic acids, in particular alpha-hydroxypropionic acid. |
| | Polyols, in particular inositol, glycerol, diglycerol, sorbitol. |
| | Polyol glycosides, in particular alginate and guar. |
| | Proteins, in particular gelatin and soluble collagen. |
| | Lipoprotides chosen from mono- or polyacylated derivatives of amino acids or of polypeptides in which the acid residue RCO contains a $C_{13}$-$C_{19}$ hydrocarbon chain, in particular palmitoylcaseinic acid, palmitoylcollagenic acid, the O,N-dipalm-itoyl derivative of hydroxyproline, sodium stearoylglutamate, collagen stearoyl tripeptide, collagen oleyl tetra- and pentapeptide, hydroxy-proline linoleate. |
| | Urea and its derivatives, in particular methylurea. |
| | Skin tissue extract, in particular that marketed by Laboratoires Serobiologiques de Nancy (LSN) under the name "OSMODYN" and containing peptides, amino acids, saccharides and 17% of mannitol. |
| | More especially, a combination of glycerol, urea and palmitoylcaseinic acid. |

TABLE I-continued

| FUNCTION | ACTIVE AGENTS WHICH ARE USABLE |
|---|---|
| Melanore-gulator: | Bergamot and citrus oils.<br>alpha-MSH and its synthetic homologues. |
| 1) suntan accelerator | Caffeine.<br>Tyrosine derivatives, in particular glucose tyrosinate and N-malyltyrosine. |
| 2) Depigmenting | Ascorbic acid or vitamin C and its derivatives, in particular Mg ascorbyl phosphate.<br>Hydroxy acids, in particular glycolic acid.<br>Kojic acid.<br>Arbutin and its derivatives.<br>Hemocyanin (copper-containing protein of the marine snail) and apohemocyanin (protein similar to the above without copper).<br>Hydroquinone and its derivatives, in particular the monoalkyl ether and the benzyl ether |
| Skin coloration (artificial suntan) | ortho-Diacetylbenzene.<br>Indoles.<br>Dihydroxyacetone.<br>Erythrulose.<br>Glyceraldehyde.<br>gamma-Dialdehydes, in particular tartraldehyde. |
| Liporegulators (slimming and anti-acne, anti-seborrhea) | Complexes of vitamins and trace elements, in particular the vitamin $B_6$/zinc complex.<br>Orizanol.<br>Azelaic acid.<br>Xanthines and alkylxanthines, in particular extract of cola, caffeine and theophylline.<br>Cyclic and acyclic adenosine monophosphate.<br>Adenosine triphosphate.<br>Ivy extract.<br>Horse chestnut extract.<br>Extracts of algae, in particular extract of red algae (*Fucus serratus*) and cytofiltrate.<br>Ginseng extract.<br>*Centella asiatica* extract (asiaticoside) containing genin and asiatic acid.<br>Thioxolone (HBT).<br>S-Carboxymethylcysteine.<br>S-Benzylcysteamine. |
| Anti-ageing and anti-wrinkle | Unsaponifiables, for example of soya bean and avocado.<br>Unsaturated fatty acids, in particular linoleic acid and linolenic acid.<br>Hydroxy acids, in particular glycolic acid.<br>Growth factors<br>Trace element/vitamin complexes, in particular $B_6$/Zn.<br>5-n-Octanoylsalicylic acid.<br>Adenosine.<br>Retinol and its derivatives, in particular retinol acetate and retinol palmitate.<br>Retinoids, in particular cis- or trans-retinoic acids and those described in Patents FR-A-2,570,377; EP-A-199,636; and EP-A-325,540 and European Patent Application 90-402072.<br>Combination of retinoids and xanthines.<br>Hydroxyproline.<br>Sialic acids.<br>The unstabilized extract of spleen, of thymus, Thiolim and bovine serum albumin sold by the company "SILAB" under the trade name "SILAB".<br>An animal placental extract, in particular 5.5% bovine placental embryonic extract in water, stabilized with 0.2% of exyl K100a (matrix).<br>Proteoglycans, especially stabilized 5% bovine tracheal cartilage proteoglycan (proteodermin).<br>Colostrum.<br>Cell oxygenation factors, in particular octacosamol. |
| Anti-UV | UV screening agents, in particular 2-ethylhexyl para-methoxycinnamate;<br>benzophenone,<br>benzylidenecamphor and their derivatives, especially 2,2',4,4',-tetrahydroxybenzophenone and 2-hydroxy-4-methoxybenzophenone-5-sulphonic acid; |

TABLE I-continued

| FUNCTION | ACTIVE AGENTS WHICH ARE USABLE |
| --- | --- |
| | para-aminobenzoic acid, |
| | dipropylene glycol salicylate, |
| | octyl salicylate, |
| | the dibenzoylmethane derivatives sold under the |
| | brand names EUSOLEX 8020 or PARSOL 1789 and |
| | the products sold under the brand names |
| | EUSOLEX 232, UNIVUL T 150, UNIVUL N 539, |
| | ESCALOL 507. |
| Keratolytic | Salicylic acid and its derivatives such as |
| | alkylsalicylic acids, in particular 5-n- |
| | octanoyl- and 5-n-dodecanoylsalicylic acids |
| | N-hexadecylpyridinium salicylate. |
| | Retinoic acid. |
| | Proteolytic enzymes, in particular trypsin, |
| | alpha-chymotrypsin, papain, bromelain and pepsin. |
| | Benzoyl peroxide. |
| | Urea. |
| | alpha-Hydroxy acids. |
| Emollient | Esters such as isopropyl adipate. |
| Anti-inflammatory | Corticoids such as β-methasone 17-acetate, |
| | indomethacin, ketoprofen, flufenamic acid, |
| | ibuprofen, dichlofenac [sic], diflunisal, |
| | fenclofenac, naproxen, piroxidam [sic] and |
| | sulindac. |
| | Glycerol monostearyl ether (batyl alcohol) and |
| | glycerol monocetyl ether (chimyl alcohol). |
| | Glycyrrhetinic acid and its salts, in particular |
| | the ammonium salt. |
| | alpha-Bisabolol (camomile extract). |
| | Shikonin. |
| | Extracts of plants such as arnica, aloe, cornflower |
| | water. |
| | Extracts of meristematic tissue, in particular |
| | oak root extract. |
| | Plankton. |
| Cooling | Menthol. |
| | Menthyl lactate. |
| Cicatrizing | Skin tree, mimosa tenui flora extract. |
| | *Centella asiatica* extract. |
| | β-Glycyrrhetinic acid. |
| | Hydroxyproline. |
| | Arginine. |
| | A placental extract. |
| | A yeast extract. |
| | Fagaramide. |
| | N-Acetylhydroxyproline. |
| | Acexamic acid and its derivatives. |
| Vasoprotective | Flavonoids, in particular rutin derivatives such |
| | as etoxazorutin and sodium rutin propylsulphonate. |
| | Plant extracts, in particular *Ginkgo biloba* oily |
| | extract and extract of horse chestnut (escin), |
| | of ivy (saponins) and of butcher's broom. |
| | alpha-Tocopherol nicotinate. |
| Anti-bacterial, | Trimethylcetylammonium bromide. |
| antifungal | Sorbic acid. |
| | Benzoyl peroxide. |
| | Cetylpyridinium chloride. |
| | Benzalkonium chloride. |
| | para-Hydroxybenzoic acid and its salts. |
| | 2-Bromo-2-nitro-1,3-propanediol. |
| | 3,4,4'-Trichlorocarbanilide. |
| | 2,4,4'-Trichloro-2-hydroxydiphenyl ether. |
| | Dehydroacetic acid. |
| | A grapefruit extract in glycerol and propylene |
| | glycol. |
| | Chlorhexidine. |
| | Hexetidine. |
| | Hexamidine. |
| Insect- | Dimethyltoluamide. |
| repellent agent | |
| Antiper- | Aluminum chlorohydrate. |
| spirant | Aluminum chloride. |
| | Sodium lactate/aluminum chlorohydroxy complex. |
| | Zirconyl chlorhydrate. |
| Deodorant | Zinc oxide |
| | Zinc ricinoleate. |
| | 2-Ethyl-1,3-hexanediol. |

TABLE I-continued

| FUNCTION | ACTIVE AGENTS WHICH ARE USABLE |
|---|---|
| | Hexachlorophene. |
| | The product sold under the brand name "IRGASAN DP 300". |
| Antidandruff | Octopyrox. |
| | Omadines. |
| | Coal tar. |
| | 1-Hydroxy-4-methyl-2,4,4-trimethyl-6-pentyl-2-pyridinone [sic]. |
| | Selenium sulphide. |
| Anti-har loss | Glucuronidase inhibitors. |
| | Muccopolysaccharides [sic]. |
| | methyl or hexyl nicotinate. |
| | Forskolin. |
| | Minoxidil. |
| | Xanthines. |
| | Retinoids. |
| Hair colorant | Oxidation bases and couplers. |
| | Direct dyes. |
| | Self-oxidizing dyes. |
| Hair bleaching agent | Hydrogen peroxide. |
| Reducing agent for permanent-waving | Thioglycolic acid. |
| | Cysteine. |
| | Cysteamine. |
| | N-Acetylcysteine. |
| | N-Acetylcysteamine. |
| | Glycerol thioglycolate. |
| Skin and hair conditioner | Cationic polymers, cations. |

The dispersions contained in the compostions according to the invention can be prepared by any known method of preparation for the preparation of amphiphilic lipid vesicles. Various modes of preparation are, for example, described in "Les liposomes en biologie cellulaire et pharmacologie" [Liposomes in cell biology and pharmacology], INSERM Publications/John Libbey Emotext, 1987, pages 6 to 18.

The vesicle dispersions according to the invention are preferably prepared by the process described below:

in a first stage, the lipid phase is prepared before forming the vesicle membrane by dissolving amphiphilic lipid (s), compounds of formula (I) and, optionally, one (or a number of) liposoluble pharmaceutically and/or cosmetically active compound(s) in a solvent and the solvent is evaporated under reduced pressure;

in a second stage, the aqueous dispersion phase is added and the mixture is homogenized mechanically by shaking and/or ultrasound, to produce the vesicle dispersion.

Homogenization is carried out at a temperature between 10° C. and 120° C., preferably between 30° and 80° C.

The compositions according to the invention can be provided in the form of gels, lotions or serums by adding, in a known way, formulation additives which have neither their own cosmetic activity nor their own dermo-pharmaceutical activity to the aqueous dispersion phase. Among these additives, there may be mentioned gelling agents, polymers, preserving agents, dyes and fragrances.

Another subject of the present invention is certain vesicle dispersions used in the compositions, according to the invention, which are novel. Consequently, a subject of the present invention is the dispersions, in an aqueous dispersion phase, of vesicles delimited by a lipid phase membrane containing at least one ionic amphiphilic lipid and/or at least one nonionic amphiphilic lipid, the said vesicles containing an encapsulated phase, characterized in that the lipid phase contains at least one compound of formula:

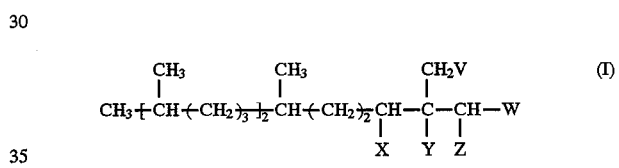

in which formula (I):

either W represents —$CH_2OH$, —COOM or —$(CH_2)_2$—COOM, where M represents H, an alkali metal or an alkaline-earth metal, in which case X, Y, Z and V, which are identical or different, represent a hydrogen atom or a hydroxyl radical, with the condition that, when W represents —$CH_2OH$ or COOM, at least one of the radicals X, Y, Z or V represents a hydroxyl radical;

or else W represents a —$CH_3$ group, in which case X, Y, Z and V represent H or —OH combined as shown in each line of the table below:

| X | Y | Z | V |
|---|---|---|---|
| OH | OH | OH | OH |
| OH | H | OH | OH |
| OH | OH | OH | H |
| H | OH | OH | OH |
| H | OH | OH | H |
| H | H | OH | OH |
| OH | H | OH | H |

A more detailed description of these transparent dispersions, which are used for the manufacture of cosmetic and/or pharmaceutical compositions, has been given above.

In order to make the subject of the invention better understood, several embodiments will now be described by way of purely illustrative and non-limiting examples.

In the examples given below, the dispersions were prepared in the following way:

1.5 g of lipid phase having the composition given in Table II below are introduced into a 100 ml round-bottomed flask and solubilization is carried out in the solvent shown in the said table. The solvent is then evaporated at 40° C. through successive stages from ambient pressure to approximately 500 Pa using a rotary evaporator.

28.5 g of a 0.02% by weight sodium azide (NaN$_3$) solution in water are added to the lipid phase film obtained during the time and at the temperature given in Table II below.

The mixture obtained is agitated using an oscillating arm shaker marketed by the company "Prolabo" under the name "Oscill 12".

The dispersion obtained, brought to a temperature of 30° C., is then treated for 2 min using an ultrasound homogenizer marketed by the company "Branson Sonic Power Co" under the name "Sonifier B 30" with the following setting:

working cycle: 50% power setting: position 5.

The following measures were carried out on the dispersion obtained:

particle size, with the apparatus marketed by the company "Coulter Electronics" under the name "Coulter N4", which operates on the quasi-elastic light scattering principle. The particle size of the vesicles is characterized by a mean diameter (d) in nanometers and a size polydispersity factor (Q). These two parameters are calculated by the method of cumulants. The measurements are carried out on dilutions containing approximately 0.3% by weight of vesicle dispersion.

The optical density of the dispersions, using a UV/visible spectrophotometer marketed by the company "Beckman" under the name "U.V. 5230", the measurement being carried out at 450 nm in a cell with a thickness of 0.2 cm after dilution of the dispersion to a quarter using a 0.02% by weight solution of sodium azide in water. The lower the optical density $OD_{450}$ obtained, the greater the transparency of the dispersion.

Comparative tests were carried out in the absence of compound of formula (I) in the lipid phase and in the presence of 1,2-hexadecanediol, which is an unbranched polyol having the same chain length as the compounds of formula (I).

The results are given in Table II below:

TABLE II

| Example No. | Composition of the lipid phase | Preparation conditions | | d (nm) | Polydispersity Q | $OD_{450}$ |
| --- | --- | --- | --- | --- | --- | --- |
| | | Solvent used in lipid phase preparation | Agitation of the mixture | | | |
| 1* | lipid 1<br>cholesterol<br>DCP | 0.825 g<br>0.600 g<br>0.075 g | 6.7 ml of di-chloromethane and 1.7 ml of methanol | 2 hours at 45° C. | 174 | 0.21 | 0.70 |
| 2 | lipid 1<br>cholesterol<br>phytanetriol<br>DCP | 0.825 g<br>0.300 g<br>0.300 g<br>0.075 g | 8.4 ml of di-chloromethane and 1.7 ml of methanol | 2 hours at 45° C. | 168 | 0.15 | 0.24 |
| 3* | lipid 1<br>cholesterol<br>1,2-hexadecanediol<br>DCP | 0.825 g<br>0.300 g<br>0.300 g<br>0.075 g | 6.7 ml of di-chloromethane and 1.7 ml of methanol | 2 hours at 45° C. | 155 | 0.22 | 0.40 |
| 4* | lipid 2<br>cholesterol<br>DCP | 0.825 g<br>0.600 g<br>0.075 g | 6.7 ml of chloroform and 1.7 ml of methanol | 2 hours at 70° C. | 178 | 0.35 | 0.67 |
| 5 | lipid 2<br>cholesterol<br>phytanetriol<br>DCP | 0.825 g<br>0.300 g<br>0.300 g<br>0.075 g | 6.7 ml of chloroform and 0.8 ml of methanol | 2 hours at 70° C. | 188 | 0.21 | 0.38 |
| 6* | lipid 2<br>cholesterol<br>1,2-hexadecanediol<br>DCP | 0.825 g<br>0.300 g<br>0.300 g<br>0.075 g | 6.7 ml of chloroform and 1.7 ml of methanol | 2 hours at 70° C. | 177 | 0.25 | 0.69 |
| 7* | lipid 3<br>cholesterol<br>DCP | 0.825 g<br>0.600 g<br>0.075 g | 6.7 ml of di-chloromethane and 1.7 ml of methanol | 2 hours at 70° C. | 129 | 0.26 | 0.10 |
| 8 | lipid 3<br>cholesterol<br>phytanetriol<br>DCP | 0.825 g<br>0.300 g<br>0.300 g<br>0.075 g | 6.7 ml of di-chloromethane and 1.7 ml of methanol | 2 hours at 70° C. | 104 | 0.28 | 0.05 |
| 9* | lipid 3<br>cholesterol<br>1,2-hexadecanediol<br>DCP | 0.825 g<br>0.300 g<br>0.300 g<br>0.075 g | 6.7 ml of di-chloromethane and 1.7 ml of methanol | 2 hours at 70° C. | 115 | 0.25 | 0.10 |
| 10* | lipid 4<br>cholesterol<br>DCP | 0.713 g<br>0.712 g<br>0.075 g | 6.7 ml of di-chloromethane | 2 hours at 70° C. | 165 | 0.31 | 0.68 |
| 11 | lipid 4<br>cholesterol<br>phytanetriol<br>DCP | 0.713 g<br>0.277 g<br>0.435 g<br>0.075 g | 6.7 ml of di-chloromethane and 1.7 ml of methanol | 2 hours at 70° C. | 140 | 0.16 | 0.17 |
| 12* | lipid 4 | 0.713 g | 6.7 ml of di- | 2 hours at | 181 | 0.15 | 0.65 |

TABLE II-continued

| Example No. | Composition of the lipid phase | Preparation conditions | | Agitation of the mixture | d (nm) | Polydispersity Q | OD$_{450}$ |
|---|---|---|---|---|---|---|---|
| | | Solvent used in lipid phase preparation | | | | | |
| | cholesterol | 0.277 g | chloromethane | 70° C. | | | |
| | 1,2-hexadecanediol | 0.435 g | and 1.7 ml of | | | | |
| | DCP | 0.075 g | methanol | | | | |
| 13 | lipid 4 | 0.713 g | 5 ml of di- | 2 hours at | 133 | 0.21 | 0.14 |
| | cholesterol | 0.277 g | chloromethane | 70° C. | | | |
| | mixture (phytanetriol + phytanetetrol) | 0.435 g | and 1.7 ml of methanol | | | | |
| | DCP | 0.075 g | | | | | |
| 14* | lipid 1 | 1.050 g | 10 ml of di- | 2 hours at | 137 | 0.22 | 0.39 |
| | cholesterol | 0.375 g | chloromethane | 45° C. | | | |
| | DCP | 0.075 g | and 2 ml of methanol | | | | |
| 15 | lipid 1 | 1.050 g | 10 ml of di- | 2 hours at | 118 | 0.21 | 0.10 |
| | phytanetriol | 0.375 g | chloromethane | 45° C. | | | |
| | DCP | 0.075 g | and 2 ml of methanol | | | | |

*does not form part of the invention

In this table, the various constituents are the following:
Lipid 1: lecithin marketed by the company "Lucas Meyer" under the name "Epikuron 200"
Cholesterol: marketed by the company "Prolabo"
DCP: sodium dicetyl phosphate
Lipid 2: hydrogenated lecithin marketed by the company "Quest International" under the name "Lecinol S 10"
Lipid 3: nonionic amphiphilic lipid: polyoxyethylenated hexadecyl alcohol containing an average of 20 ethylene oxide units, marketed by the company "ICI Atlas" under the name "Brij 58"
Lipid 4: nonionic amphiphilic lipid of formula:

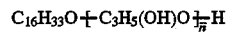

where —C$_3$H$_5$(OH)O— is represented by the following structures taken as a mixture or separately:

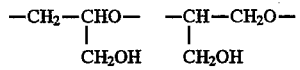

and $\bar{n}$ is a mean statistical value equal to 3
Mixture (phytanetriol+phytanetetrol): approximately 1/1 by weight mixture of phytanetriol and a tetrol consisting of the following isomers taken as a mixture or separately:

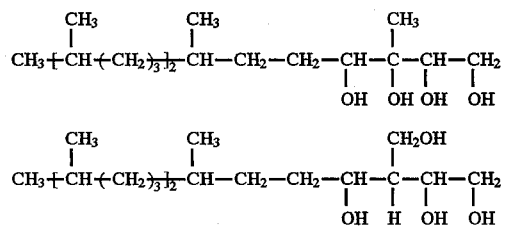

We claim:
1. A composition comprising, in an aqueous dispersion phase, a dispersion of lipid vesicles encapsulating an aqueous phase, said lipid vesicles comprising a lipid phase containing (a) an ionic amphiphilic lipid or (b) a nonionic amphiphilic lipid, or a mixture of (a) and (b), together with (c) a compound having the formula

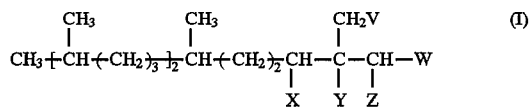

wherein
(a) W represents —CH$_2$OH, —COOM or —(CH$_2$)$_2$—COOM, wherein M represents H, alkali metal or alkaline earth metal and X, Y, Z and V, each independently, represent hydrogen or hydroxyl, with the proviso that when W represents —CH$_2$OH at least one of X, Y, Z or V represents hydroxyl, or
(b) W represents —CH$_3$ and X, Y, Z and V represent H or OH combined as shown in each line of the table below:

| X | Y | Z | V |
|---|---|---|---|
| OH | OH | OH | OH |
| H | OH | OH | H |
| H | H | OH | OH |
| OH | H | OH | H | with the proviso that the compound of formula (I) is not phytanetriol; 3-hydroxymethyl-7,11-15-trimethyl-1,2,4-trihydroxyhexadecane; 5,9,13,17-tetramethyloctadecanoic acid or 3,7,11,15 tetramethyloctadecanoic acid.

2. The composition of claim 1 wherein said compound of formula (I) represents from 5% to 90% by weight of said lipid vesicles.

3. The composition of claim 1 wherein the lipid of said vesicles is a nonionic amphiphilic lipid selected from the group consisting of
(1) a linear or branched glycerol derivative having the formula

wherein
—C$_3$H$_5$(OH)O—, jointly or separately represents —CH$_2$CHOHCH$_2$O—,

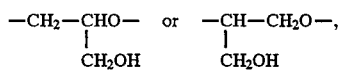

$\bar{n}$ has a mean statistical value ranging from 1 to 6, or when $\bar{n}$ represents 1 or 2 then —C$_3$H$_5$(OH)O— represents —CH$_2$CHOH—CH$_2$O—, R$_0$ represents (a) an aliphatic, linear or branched, saturated or unsaturated chain containing 12 to 30 carbon atoms or a lanolin alcohol hydrocarbon chain, or the residue of a long chain alpha-diol, (b) R$_1$CO wherein R$_1$ represents an aliphatic, linear or branched, radical having 11 to 29 carbon atoms, or

wherein

R$_2$ represents (a) or (b) defined above for R$_0$ and wherein —OC$_2$H$_3$(R$_3$)- represents, jointly or separately,

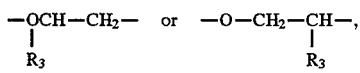

wherein R$_3$ represents (a) defined above for R$_0$;

(2) a linear or branched polyglycerol ether having two fatty chains;

(3) a diol containing a fatty chain;

(4) a fatty oxyethylenated alcohol, a fatty non-oxyethylenated alcohol, an oxyethylenated phytosterol, a non-oxyethylenated phytosterol, an oxyethylenated sterol or a non-oxyethylenated sterol;

(5) an oxyethylenated ether of a polyol, a non-oxyethylenated ether of a polyol, an oxyethylenated ester of a polyol or a non-oxyethylenated ester of a polyol, wherein the ethylene oxide chain is linear or cyclic;

(6) a natural or synthetic glycolipid, an ether or ester of a mono- or polysaccharide or an ether or ester of glucose;

(7) a hydroxyamide having the formula

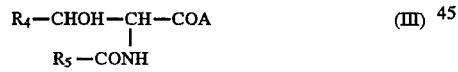

wherein

R$_4$ represents alkyl or alkenyl having 7 to 21 carbon atoms,

R$_5$ represents a saturated or unsaturated hydrocarbon having 7 to 31 carbon atoms, COA represents a member selected from the group consisting of

wherein B is an alkyl radical derived from a mono- or polyhydroxylated, primary or secondary amine; and R$_6$ represents hydrogen or methyl, and (ii) —COOZ wherein Z represents a polyol residue having 3 to 7 carbon atoms;

(8) a natural or synthetic ceramide;

(9) an oxyethylenated fatty amine or a dihydroxyalkylamine; and

(10) a glycerol derivative having the formula

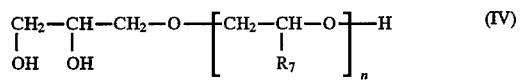

wherein

R$_7$ represents linear C$_{14}$–C$_{18}$ alkyl or a —CH$_2$A group wherein A is —OR$_{14}$, R$_{14}$ representing linear C$_{10}$–C$_{18}$ alkyl and n represents a mean statistical value greater than 1 and at most equal to 3 and when R$_7$=—CH$_2$A, n can also represent a true, non-statistical value equal to 2.

4. The composition of claim 1 wherein the lipid of said vesicles is an ionic amphiphilic lipid selected from the group consisting of (1) an anionic amphiphilic lipid selected from the group consisting of a natural phospholipid, a chemically or enzymatically modified phospholipid, a synthetic phospholipid, a compound having the formula

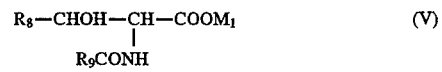

wherein

R$_8$ represents alkyl or alkenyl having 7 to 21 carbon atoms,

R$_9$ represents a saturated or unsaturated C$_7$–C$_{31}$ hydrocarbon radical and M$_1$ represents H, Na, K, NH$_4$ or a substituted ammonium ion derived from an amine;

(2) an anionic compound selected from the group consisting of a phosphoric ester of a fatty alcohol, heptylnonylbenzenesulfonic acid, cholesterol acid sulfate or an alkaline salt thereof, cholesterol acid phosphate or an alkaline salt thereof, a lysolecithin, an alkyl sulfate and a ganglioside; and (3) a cationic amphiphilic lipid selected from the group consisting of a quaternary ammonium derived compound having the formula

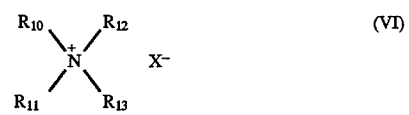

wherein

R$_{10}$ and R$_{11}$, each independently, represent C$_{12}$–C$_{20}$ alkyl and R$_{12}$ and R$_{13}$, each independently, represent C$_1$–C$_4$ alkyl;

a long chain amine or a quaternary ammonium derivative thereof; and a long chain amino alcohol ester or a salt thereof or a quaternary ammonium derivative thereof.

5. The composition of claim 1 wherein said aqueous dispersion phase is selected from the group consisting of water, a mixture of water and a C$_1$–C$_7$ alcohol, a mixture of water and a C$_1$–C$_5$ alkyl polyol, and mixtures thereof.

6. The composition of claim 1 wherein said lipid vesicles are present in an amount ranging from 0.01 to 50 percent by weight based on the total weight of said dispersion.

7. The composition of claim 1 where in said lipid phase said ionic amphiphilic lipid (a) or said nonionic amphiphilic lipid (b) or a mixture thereof is present in an amount ranging from 10 to 95 percent by weight relative to the total weight of said lipid phase.

8. The composition of claim 1 where in said lipid phase said ionic amphiphilic lipid (a) or said nonionic amphiphilic lipid (b) or a mixture thereof is present in an amount ranging from 40 to 90 percent by weight relative to the total weight of said lipid phase.

9. The composition of claim 1 wherein said lipid vesicles have a size ranging from 20 to 3000 nm.

10. The composition of claim 1 wherein said lipid vesicles have a size ranging from 20 to 500 nm.

11. The composition of claim 1 further comprising an active principle having cosmetic action, an active principle having pharmaceutic action, or a mixture thereof.

12. The composition of claim 1 wherein said lipid phase of said lipid vesicles further comprises at least one cosmetically active liposoluble compound or pharmaceutically active liposoluble compound, or a mixture thereof.

13. The composition of claim 1 wherein said aqueous phase encapsulated in said lipid vesicles further comprises at least one cosmetically active water-soluble compound, or a pharmaceutically active water-soluble compound, or a mixture thereof.

14. The composition of claim 1 wherein said aqueous dispersion phase further comprises at least one cosmetically active water-soluble compound or a pharmaceutically active water-soluble compound, or a mixture thereof.

15. The composition of claim 1 in the form of a gel or lotion.

* * * * *